United States Patent [19]
Mezō

[11] Patent Number: 5,823,979
[45] Date of Patent: Oct. 20, 1998

[54] DEVICE FOR STABILIZING JOINTS OF THE LIMBS

[76] Inventor: Róbert Mezō, Kresz Géza u. 17. III.5., H-1134 Budapest, Hungary

[21] Appl. No.: 875,626

[22] PCT Filed: Jan. 24, 1996

[86] PCT No.: PCT/HU96/00004

§ 371 Date: Jul. 24, 1997

§ 102(e) Date: Jul. 24, 1997

[87] PCT Pub. No.: WO96/22749

PCT Pub. Date: Aug. 1, 1996

[30] Foreign Application Priority Data

Jan. 24, 1995 [HU] Hungary ............... P9500207

[51] Int. Cl.$^6$ ............... A61F 5/00
[52] U.S. Cl. ............... 602/16; 602/26
[58] Field of Search ............... 602/5, 16, 20, 602/23, 26

[56] References Cited

U.S. PATENT DOCUMENTS 2,545,843 3/1951 Cohan .
3,848,326 11/1974 Lonardo .
4,054,130 10/1977 Franke .

*Primary Examiner*—Linda C. Dvorak
*Attorney, Agent, or Firm*—Spencer & Fran

[57] ABSTRACT

The device according to the invention comprises a hinge for the joint of a limb including two rods being connected by a hinge having two elements arranged on a common shaft and a locking element. The mating faces of the hinge elements are provided with perpendicular protrusions and indentations, wherein the protrusions and indentations are parallel ribs and grooves, respectively. One of the hinge elements is arranged on the shaft to rotate freely, the other hinge element is fitted onto an outer thread on the shaft while the locking element is firmly anchored on the shaft.

7 Claims, 1 Drawing Sheet

DEVICE FOR STABILIZING JOINTS OF THE LIMBS

BACKGROUND OF THE INVENTION

The present invention relates to a device for stabilizing joints of the limbs, consisting of supporting rods attached to the limbs, a hinge between the rods, two coaxial hinge elements and a locking element. Under a number of conditions there is a need to stabilize a joint of the limbs. Often following illness or surgery the joints connecting the limbs cannot be stressed sufficiently. In other cases following surgery, involving amputation of the limbs, the connection of the prostheses must be constructed to produce a movement similar to that of the original joint of the limb. In both cases the device is constructed—with the recovery of the patient in mind—so, that when needed (for instance when sitting down), adjustment of the joint is possible, meanwhile giving ample support to the limb when fastened.

These devices are most commonly constructed so that two rods are joined with a so called latch-joint or hinge, making it possible for the two rods to be fixated in a given position. The latch-joint is constructed in a way, that an element of the latch, which is connected to one part of the joint, can be inserted into a slot of the other part of the joint so that it can be fixated in a given position. The latch can be disconnected by pulling the latch, which is secured by a spring, out of the slot, thus making movement of the joints possible.

The described system, called the Hessing apparatus, is still used today as an improvement of the so called Hoffa-band [Dr. Gyula Dollinger: "Inflammation, rigidity and shrinkage of the hip joints" (pages 60–62)]. Another common method is described by 1994–95 catalogue of the German—Otto Bock orthopaedic and aid-device manufacturer. The apparatus shown on the 48th page has the rods stabilizing the paralysed limb, connected by a hinge. Relative movement of the joint is controlled by an arm that inserts for stabilize, or removes for movement of a wedge.

The described systems share a common problem: they do not offer an entirely satisfying degree of safety. This way the users, people already greatly hindered in their movement, are even more prone to injury. Another great drawback is, because the devices are machined or precision cast from metal, that they are heavy and have a very small supporting area, thus wearing-out very quickly. Due to the wear they also become even less safe.

The object of the present invention is to eliminate the mentioned problems and to provide a simple, safe and wear resistant design which can stabilize the injured or healing joints.

BRIEF SUMMARY OF THE INVENTION

Accordingly, the invention is a device comprising two rods to be secured to the limb, said rods being connected by a hinge consisting of two elements arranged on a common shaft and a locking element, wherein the mating faces of the hinge elements are provided with perpendicular protrusions and indentations, respectively. The indentations are of the same shape as the protrusions and the contours of both the protrusions and the indentations are other than rings coaxial with the shaft; one of the hinge elements is arranged on the shaft to rotate freely, the other hinge element is fitted onto an outer thread on said shaft, meanwhile the locking element is firmly anchored on the shaft.

The hinge elements are preferably discs, wherein the protrusions on one disc are trapezoid shaped parallel ribs, while the indentations on the other disc are grooves of the same shape and arrangement.

The discs may be of circular shape and made of plastics and the shaft may be made of metal.

Preferably, the locking element is a lever and the shaft is provided with a multiple coarse pitch square thread.

With this device, one of the hinge elements can be moved from the other one by way of the locking element, so that there is a distance between the elements that usually are in contact with each other this way ensuring independent movement of the two elements.

When the elements are moved again to contact each other, they can not rotate with respect to each other as the protrusions and the indentations are mating each other.

The basis for the invention is the fact that the moving parts of the device are put out to a lot less stress if the fixation isn't done on the small peripherial surfaces of the elements, but on the larger area of the front surfaces. Accordingly, locking does not occur in a radial direction but in a plane perpendicular thereof. This design not only reduces the stress and thus the wear to the joints, but makes the device a lot safer in the locked position, and it's use easier. The chances of accidents are minimalized, which is crucial in serving it's purpose.

BRIEF DESCRIPTION OF THE DRAWINGS

The details of the invention are shown in the accompanying drawings, in which.

DETAILED DESCRIPTION OF THE INVENTION

Figure 1:
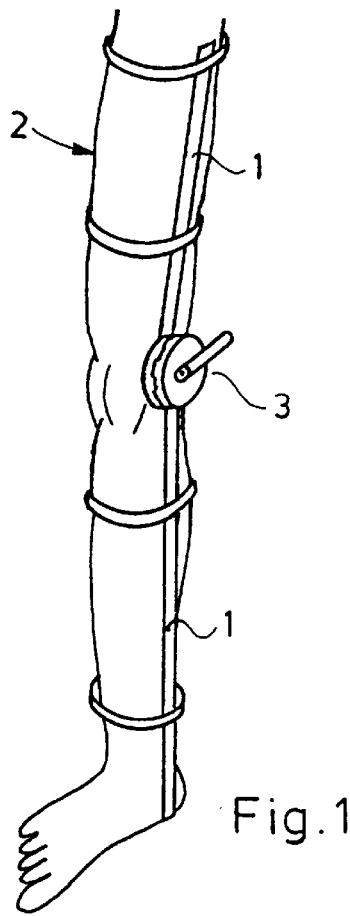
FIG. 1 is a perspective view of the device.

FIG. 1 shows the device in use, fastened to a limb. The rods 1 are fastened to the limb 2 above and below the knee of the user and are connected by hinge 3. The hinge 3 is locked in the shown position, thus the rods 1 and hinge 3 create a single rigid unit.

Figure 2:
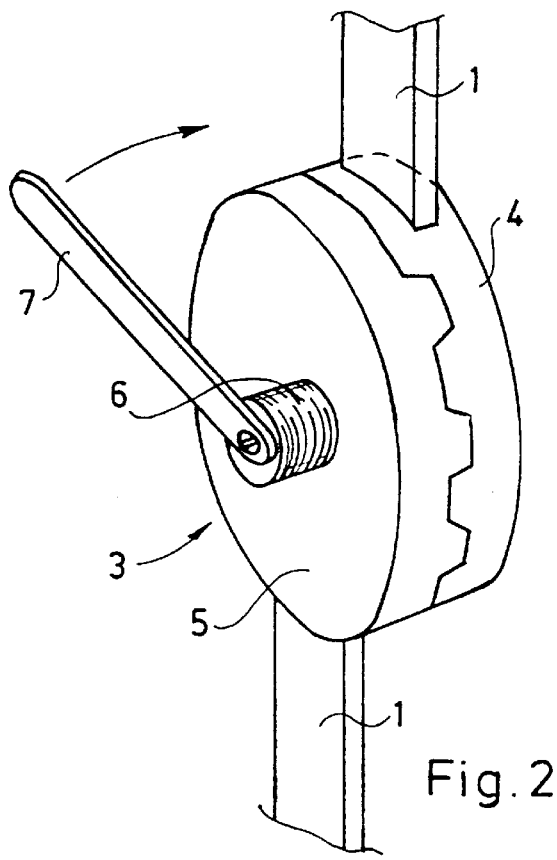
FIG. 2 is a perspective view of the hinge.

FIG. 2 shows the midsection of the device consisting of the hinge 3 with elements 4 and 5 and a shaft 6 with a lever 7 as locking element.

Figure 3:
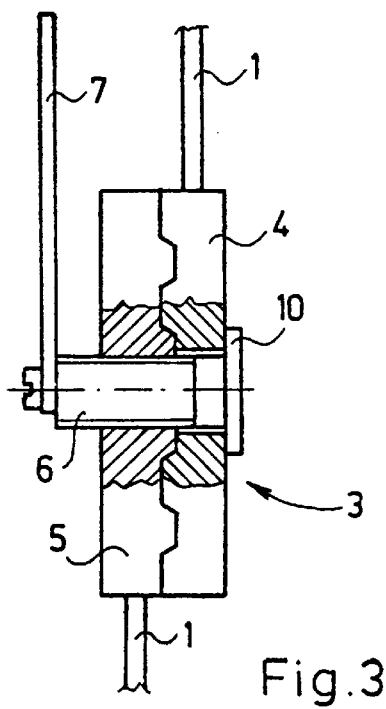
FIG. 3 is a cross section of the fastened joint illustrated in FIG. 2.
Figure 4:
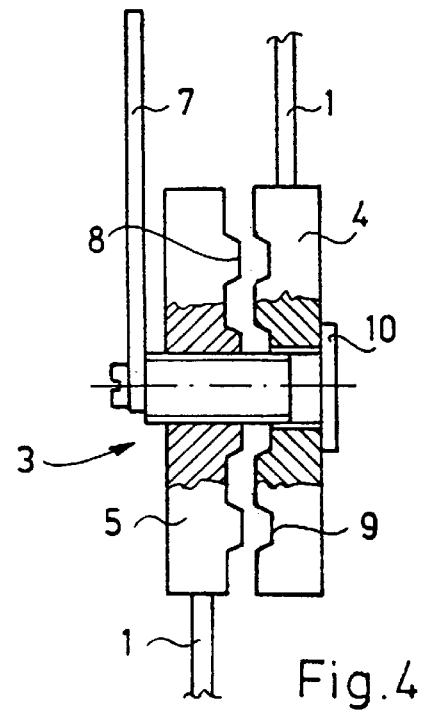
FIG. 4 is a cross section of the hinge illustrated in FIG. 3, in a position the elements can rotate.

FIGS. 3 and 4 show the details of the trapezoid shaped mateble ribs 8 and slots 9 of the hinge elements 4 and 5, respectively. The ribs 8 and grooves 9 that run across the mating faces of the hinge elements 4 and 5 are parallel with the diameter of the hinge elements.

Hinge element 4 is fitted onto the shaft 6 so it can rotate freely and is supported by rim 10.

The central bore in hinge element 5 is threaded corresponding to the outer thread of shaft 6. This way when lever 7 is turned, element 4 can recess and the mating grooves 9 and ribs 8 prevent possible rotation of the hinge elements.

Shaft 6 is preferably provided with a multiple coarse pitch square thread. This way hinge element 5 can recess, by a slight turn of lever 7, from the other hinge element 4. At this time the rods 1 can move freely, and the leg shown on FIG. 1 can be bent in order to sit down.

Hinge elements 4 and 5 of the joint can mate, in a similar way, by turning the lever 7 in the opposite direction.

Naturally, the present invention may be applied in many different ways and the scope of the invention is not to be taken as limited by the description of the above preferred specific device. It is obvious that the locking lever can be substituted by a dial or any other structural element. The joints do not have to consist of discs, grooves and ribs, but other connecting configurations my also be used. The threaded shaft can also be manufactured as a separate unit.

I claim:

1. In a device for supporting a joint of a limb, including two rods to be secured to the limb, said rods being connected by a hinge having two elements arranged on a common shaft and a locking element, wherein mating faces of the hinge elements are provided with perpendicular protrusions and indentations, respectively, the indentations are of the same shape as the protrusions and one of the hinge elements is arranged on the shaft to rotate freely, the other hinge element is fitted onto an outer thread on said shaft, the locking element being firmly anchored on the shaft; the improvement wherein the protrusions and indentations are parallel ribs and grooves, respectively and the thread on the locking element is a coarse pitch thread.

2. The device as claimed in claim 1, wherein the hinge elements are discs, and wherein the parallel ribs on one disc and the parallel grooves on the other disc have trapezoid-shaped cross sections.

3. The device as claimed in claim 2, wherein the discs are of circular shape and made of plastic.

4. The device as claimed in claim 1, wherein characterized in that the shaft is made of metal.

5. The device as claimed in claim 1, wherein characterized in that the locking element is a lever.

6. The device as claimed in claim 1, wherein the outer thread of the shaft is a multiple thread.

7. The device as claimed in claim 6, wherein the thread is a square thread.

* * * * *